US010782708B2

(12) United States Patent
Togliatti

(10) Patent No.: US 10,782,708 B2
(45) Date of Patent: Sep. 22, 2020

(54) AUTOMATIC SHUTOFF CONTINUOUS POSITIVE AIR PRESSURE SYSTEM

(71) Applicant: International Business Machines Corporation, Armonk, NY (US)

(72) Inventor: Dante Togliatti, San Diego, CA (US)

(73) Assignee: International Business Machines Corporation, Armonk, NY (US)

(*) Notice: Subject to any disclaimer, the term of this patent is extended or adjusted under 35 U.S.C. 154(b) by 83 days.

(21) Appl. No.: 16/183,251

(22) Filed: Nov. 7, 2018

(65) Prior Publication Data
US 2020/0142434 A1  May 7, 2020

(51) Int. Cl.
G05D 7/06 (2006.01)
G16H 20/30 (2018.01)

(52) U.S. Cl.
CPC .............. G05D 7/06 (2013.01); G16H 20/30 (2018.01)

(58) Field of Classification Search
CPC .................................. G05D 7/06; G16H 20/30
See application file for complete search history.

(56) References Cited

U.S. PATENT DOCUMENTS

| 4,345,592 | A | 8/1982 | Giorgini et al. |
| 4,345,593 | A | 8/1982 | Sullivan |
| 4,430,995 | A * | 2/1984 | Hilton ................ A61M 16/107 128/204.21 |
| 4,590,951 | A * | 5/1986 | O'Connor ............ A62B 18/006 128/204.23 |
| 4,886,056 | A * | 12/1989 | Simpson .............. A62B 18/006 128/201.25 |
| 5,503,146 | A | 4/1996 | Froehlich et al. |
| 6,240,921 | B1 | 6/2001 | Brydon et al. |
| 7,087,027 | B2 * | 8/2006 | Page .................... A61B 5/0816 600/537 |
| 7,305,988 | B2 * | 12/2007 | Acker .................. A61B 5/0836 128/204.18 |
| 9,655,766 | B2 * | 5/2017 | Hyde ..................... A61B 7/003 |
| 9,707,121 | B2 * | 7/2017 | Hyde ................... A61B 5/4836 |
| 10,548,760 | B2 * | 2/2020 | Hyde ................... A61B 5/4836 |
| 2006/0174883 | A1 | 8/2006 | Aylsworth et al. |
| 2017/0274169 | A1 * | 9/2017 | Kurtz ................ A61M 16/0683 |
| 2017/0303822 | A1 * | 10/2017 | Allsworth .............. A61B 5/082 |

OTHER PUBLICATIONS

ResMed Ltd., "ResMed AirSense 10 User Guide." Distributed by ResMed Corp, 9001 Spectrum Center Boulevard, San Diego CA 92123 USA, © 2014 ResMed, Ltd.

* cited by examiner

Primary Examiner — Charles R Kasenge
(74) Attorney, Agent, or Firm — Peter K. Suchecki

(57) ABSTRACT

Provided is an automatic shutoff continuous positive air pressure (CPAP) system. The automatic shutoff CPAP system includes an air pump and a processor operably connected to a sensor disposed in headgear. The processor monitors data generated from the sensor. The processor compares the generated data from the sensor to a shutoff threshold. The processor determines that the headgear has been pulled away from a face of a user when the generated data satisfies the shutoff threshold. The processor deactivates the air pump of the CPAP system in response to determining the air mask has been pulled away from the face of the user.

14 Claims, 9 Drawing Sheets

US 10,782,708 B2

AUTOMATIC SHUTOFF CONTINUOUS POSITIVE AIR PRESSURE SYSTEM

BACKGROUND

The present disclosure relates generally to the field of continuous positive air pressure (CPAP) machines, and more specifically, to an automatic shutoff CPAP system for deactivating an air pump using a sensor.

CPAP machines are used to treat sleep apnea. The CPAP machine requires a user to wear headgear having an air delivery system that delivers a continuous air pressure to the user's oral cavity. The air delivery system may be in the form of an oral mask or a nasal pillow. The CPAP machine supplies continuous air to the air mask or pillow through a tube that is connected to an air pump. The continuous air is delivered to the user's oral cavity in order to keep the oral cavity and associated tissues from closing while the user is sleeping. The continuous airflow provided by the CPAP machine prevents the user from snoring and experiencing difficulty in breathing that results in sleep apnea.

SUMMARY

Embodiments of the present disclosure include a method, computer program product, and an automatic shutoff CPAP system for deactivating an air pump using a sensor. The automatic shutoff CPAP system includes an air pump and a processor operably connected to a sensor disposed in headgear. The processor monitors data generated from the sensor. The processor compares the generated data from the sensor to a shutoff threshold. The processor determines that the headgear has been pulled away from a face of a user when the generated data satisfies the shutoff threshold. The processor deactivates the air pump of the CPAP system in response to determining the air mask has been pulled away from the face of the user.

The above summary is not intended to describe each illustrated embodiment or every implementation of the present disclosure.

BRIEF DESCRIPTION OF THE DRAWINGS

The drawings included in the present disclosure are incorporated into, and form part of, the specification. They illustrate embodiments of the present disclosure and, along with the description, serve to explain the principles of the disclosure. The drawings are only illustrative of typical embodiments and do not limit the disclosure.

Figure 1:
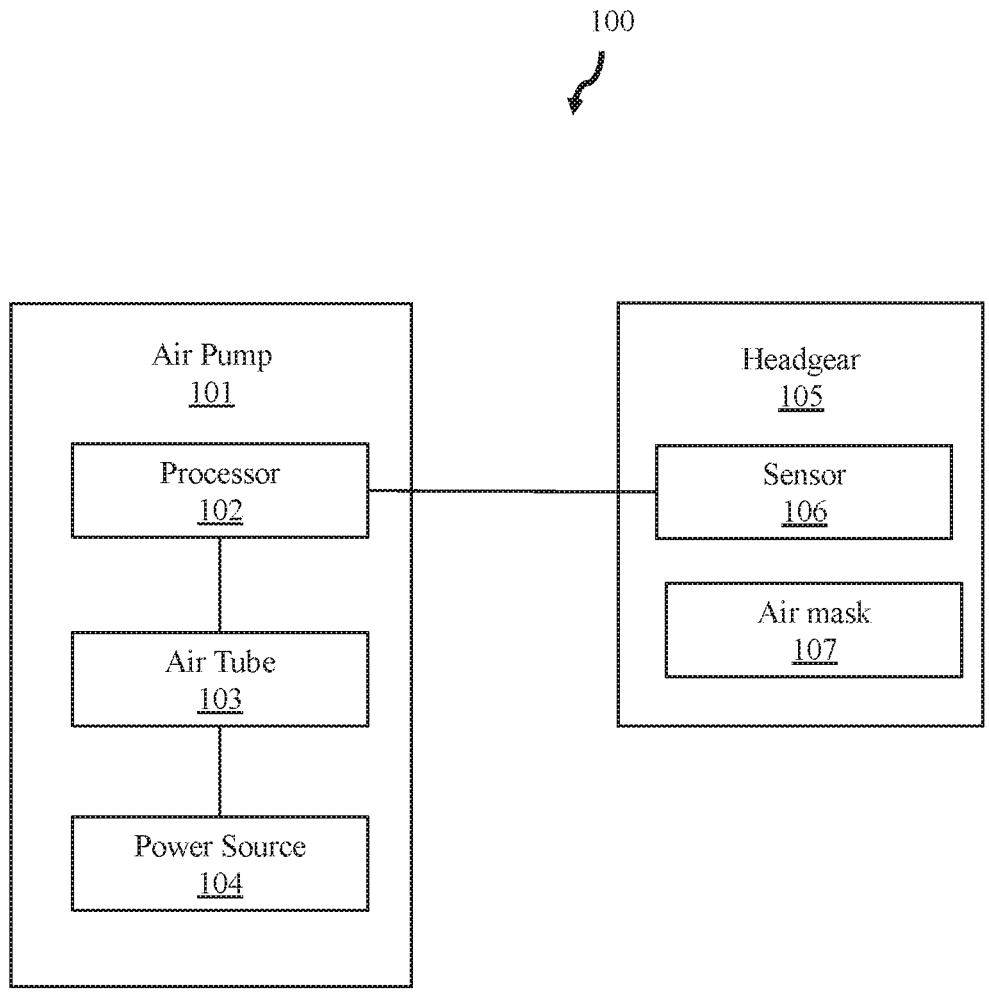
FIG. 1 illustrates a block diagram of the automatic shutoff CPAP system, in accordance with embodiments of the present disclosure.

While the embodiments described herein are amenable to various modifications and alternative forms, specifics thereof have been shown by way of example in the drawings and will be described in detail. It should be understood, however, that the particular embodiments described are not to be taken in a limiting sense. On the contrary, the intention is to cover all modifications, equivalents, and alternatives falling within the spirit and scope of the disclosure.

DETAILED DESCRIPTION

Aspects of the present disclosure relate to the field of continuous positive air pressure (CPAP) machines, and more particularly to an automatic shutoff CPAP system for deactivating an air pump using a sensor. While the present disclosure is not necessarily limited to such applications, various aspects of the disclosure may be appreciated through a discussion of various examples using this context.

A CPAP machine delivers a continuous positive air pressure from an air pump to the user's oral cavity via an air mask. The continuous air pressure keeps the user's oral cavity and associated tissues from closing while the user is sleeping. The continuous airflow provided by the CPAP machine prevents the user from snoring and experiencing difficulty in breathing that results in sleep apnea. However, a user may experience inconvenience when operating a standard CPAP machine. In some instances, the headgear may be intentionally or unintentionally removed from the head prior to deactivating the air pump of the system causing a loud and sudden rush of compressed air to disperse from the air mask. The loud and sudden rush of compressed air may disorient or disturb the user or the user's partner during sleep. Further the compressed air may jettison any bacteria from within the air mask into the air causing an unsanitary environment.

Embodiments of the present disclosure provide an automatic shutoff CPAP system that automatically deactivates the air pump when the headgear is removed by the user. The system includes one or more sensors disposed in the headgear. The sensors send data to a processor, wherein the processor determines, based on the data, whether to deactivate the air pump.

In some embodiments, the one or more sensors are configured as tension sensors embedded in the straps or headband of the headgear. In this way, when a user removes the air mask the straps of the headgear are stretched outwardly such that the embedded tension sensors expand. Data generated from the expanded tension sensors is analyzed by the processor which deactivates the air pump when the mask is removed.

In another embodiment, the sensor is an air pressure sensor disposed within the air mask of the headgear. The air pressure sensor may measure the pressure (or pressure gradient) at or near the user's mouth or nose, or elsewhere within the air mask. The processor receives data from the air pressure sensor and deactivates the air pump when air pressure data drops below a predetermined threshold (e.g., when the mask is removed).

With reference now to FIG. 1, shown is a block diagram of an automatic shutoff CPAP system 100, in accordance with embodiments of the present disclosure. Automatic shutoff CPAP system 100 includes an air pump 101 having a processor 102 and an air tube 103 operably connected to headgear 105. The air pump 101 includes power source 104. The power source 104 may be any type of suitable power source, such as a wired electrical connection or a battery. The headgear 105 includes one or more sensors 106 configured to send sensor data to the processor 102. In some embodiments, sensor data may be in the form of tension data, air pressure data, or voltage. The headgear 105 includes an air mask 107 (e.g., nasal pillow or oral mask) configured to send air through a user's nasal or oral cavity. The processor 102 is configured to analyze the data received from the sensor 106 to determine if the air pump 101 should be deactivated, as described in FIG. 2. In some embodiments, processor 102 may be substantially similar to, or the same as, computer system 1101 described in FIG. 7. In some embodiments, processor 102 may be configured as a microprocessor or a microcontroller. In some embodiments, one or more processors 102 may be included in the CPAP system 100. For example, processor 102 may be disposed within the headgear 105 and/or the air pump 101.

Figure 2:
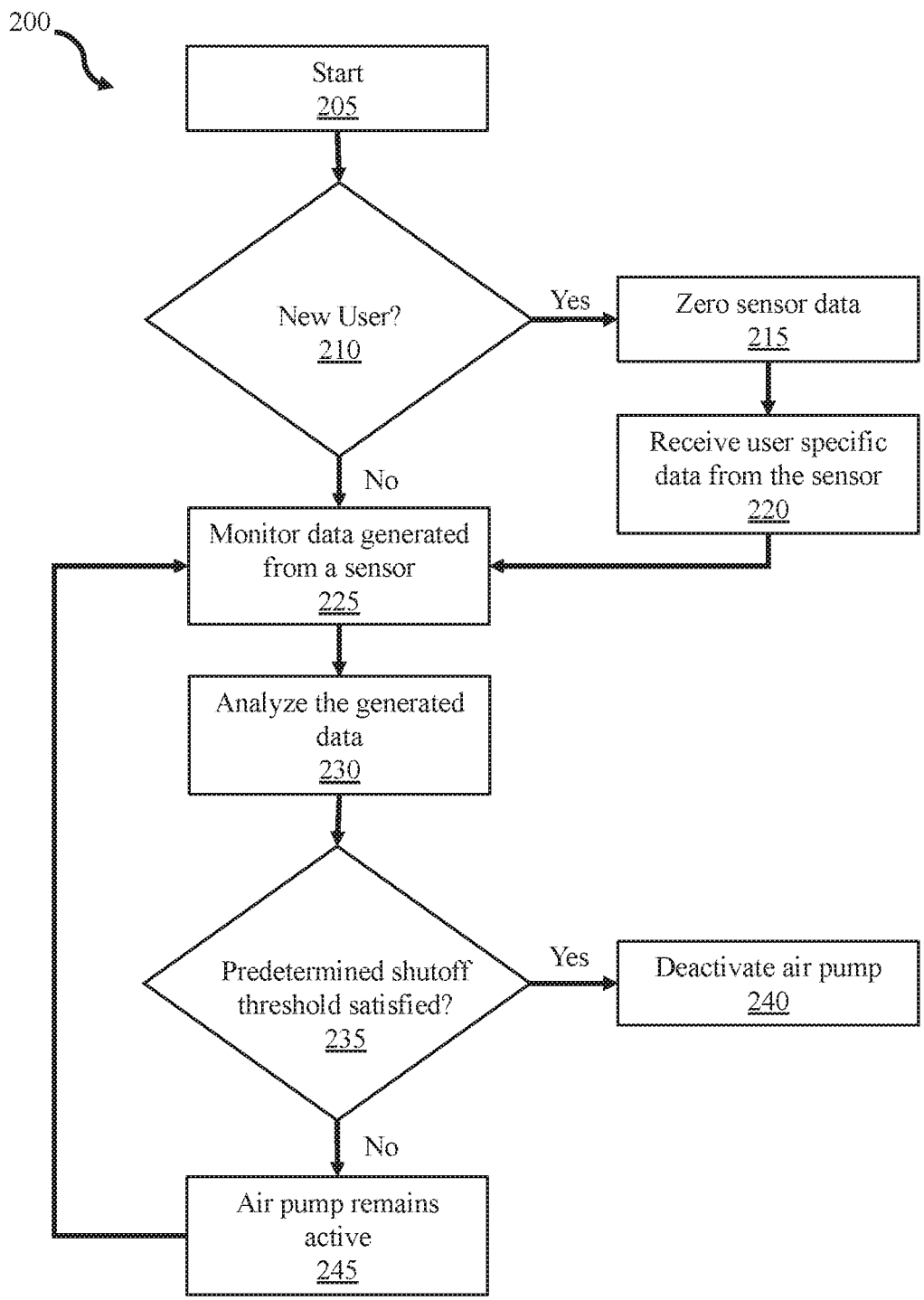
FIG. 2 illustrates a flow diagram of an example process for deactivating the automatic shutoff CPAP system, in accordance with embodiments of the present disclosure.

Referring now to FIG. 2, shown is a flow diagram of an example process 200 for deactivating the automatic shutoff CPAP system, in accordance with embodiments of the present disclosure. The process 200 may be performed by processing logic that comprises hardware (e.g., circuitry, dedicated logic, programmable logic, microcode, etc.), software (e.g., instructions run on a processor 102 to perform hardware simulation), firmware, or a combination thereof. In some embodiments, the process 200 is a computer-implemented process. The process 200 may be performed by processor 102 exemplified in FIG. 1.

In order for process 200 to begin, a user must first place the headgear, including the air mask, on the user's head in an operational position (e.g., air mask secured over the user's oral or nasal cavity and straps of the headgear in place around the user's head). Once in place, the user can selectively activate the CPAP system via an actuator (e.g., button, toggle switch, etc.) located on the air pump. This is illustrated by step 205. Once the system is activated, the processor will begin monitoring data generated from the sensor within the headgear. This is illustrated by step 225. In some embodiments, the user may activate the CPAP system prior to placing the headgear on the user's head. For example, headgear equipped with a tension sensor may include an electrical trigger that activates the tension sensor when the headgear is first placed on the user's head when the air pump is already activated. In this way, when the air pump is activated and the headgear is initially placed on the user's head, the first expansion of the tension sensor will only activate the sensor and not deactivate the air pump.

In some embodiments, the CPAP system may determine whether there is a new user. This is illustrated in step 210. If a new user is utilizing the system for the first time, the user may first zero the sensor data to generate accurate sensor data. This is illustrated in step 215. In other words, the user may establish a baseline sensor value (e.g., based on the size of the user's head, the air pressure at the mask when the user is wearing the device, etc.) that indicates values of the sensor when the user is wearing the mask. In some embodiments, the user may zero the system by pressing an operably connected button disposed on the mask (shown as switch 308 in FIG. 3). Once zeroed, the processor may receive user specific data from the sensor. This is illustrated in step 220. For example, a CPAP system equipped with a tension sensor within the straps of the headgear may be zeroed in order to accommodate for a specific head size. In this way, the tension sensor data may accurately account for variable tension corresponding to differing sizes of heads. In another example, a CPAP system equipped with an air pressure sensor within the air mask may be zeroed to account for variable air passageway pressure of the user in order to obtain accurate air pressure sensor data. In some embodiments, it may be necessary to zero the system for each use regardless of the user.

Once the CPAP system is zeroed for a new user or activated by the user, the process 200 continues by monitoring data generated from the sensor. This is illustrated in step 225. In some embodiments, the data generated by the sensor may be in the form of tension sensor data, air pressure sensor data, or voltage data, depending on the type of sensor used. The process 200 continues by analyzing the generated data. This is illustrated in step 230. The data is analyzed to determine if a shutoff threshold has been satisfied. This is illustrated in step 235. If the shutoff threshold has been satisfied, the processor may determine that the user has removed the mask from their face. For example, if the sensor is configured as a tension sensor, the tension sensor data may be analyzed to determine if the maximum tension threshold (e.g., shutoff threshold) has been exceeded, indicating that the tension sensors have been stretched to allow the user to remove the mask. Alternatively, if the sensor is configured as an air pressure sensor, the air pressure data may be analyzed to determine if the air pressure data has dropped below a minimum air pressure threshold (e.g., shutoff threshold), indicating that the mask has been removed and that the air is being allowed to flow freely.

If the processor determines that the shutoff threshold has been satisfied, the processor will instruct the air pump to deactivate. This is illustrated in step 240. For example, if the user removes the headgear having tension sensors embedded in the straps, the tension data will increase when the tension sensors are expanded. In this way, the tension data generated will exceed the predetermined tension threshold and the processor will instruct the air pump to deactivate. However, if the processor determines that the analyzed data has not exceeded the predetermined threshold, then the air pump remains active. This is illustrated in step 245. For example, if the user moves around during use (e.g., movements during sleep) when wearing headgear having tension sensors embedded in the straps, slight variations or increases in tension data resulting from the movement of the user will not exceed the predetermined threshold, thus keeping the air pump active during use. The processor will continue to monitor the data generated from the sensor as illustrated in step 225 until the data exceeds the predetermined data threshold (e.g., when the user removes the air mask).

In some embodiments, the user may be required to manually set the shutoff threshold while wearing the air mask. Setting the shutoff threshold may be performed by slightly pulling the air mask away from the user's face and pressing an operably connected switch disposed on the air mask or system. Setting the shutoff threshold provides the processor with a data point that once satisfied, causes the processor to instruct the pump to deactivate. Some users may desire different shutoff thresholds depending on their preference and sensor type. For example, a user that is a restless sleeper may set the shutoff threshold of a tension sensor at a higher maximum to prevent the air pump from deactivating as a result of slight tension increases in the headgear due to body movement when sleeping. Alternatively, a peaceful sleeper may want a lower shutoff threshold for a tension sensor to account for little movement of the headgear and air mask during sleep. Similarly, a user utilizing an air pressure sensor, may set a lower air pressure threshold to account for slight pressure drops resulting from air mask movements during sleep.

Figure 3:
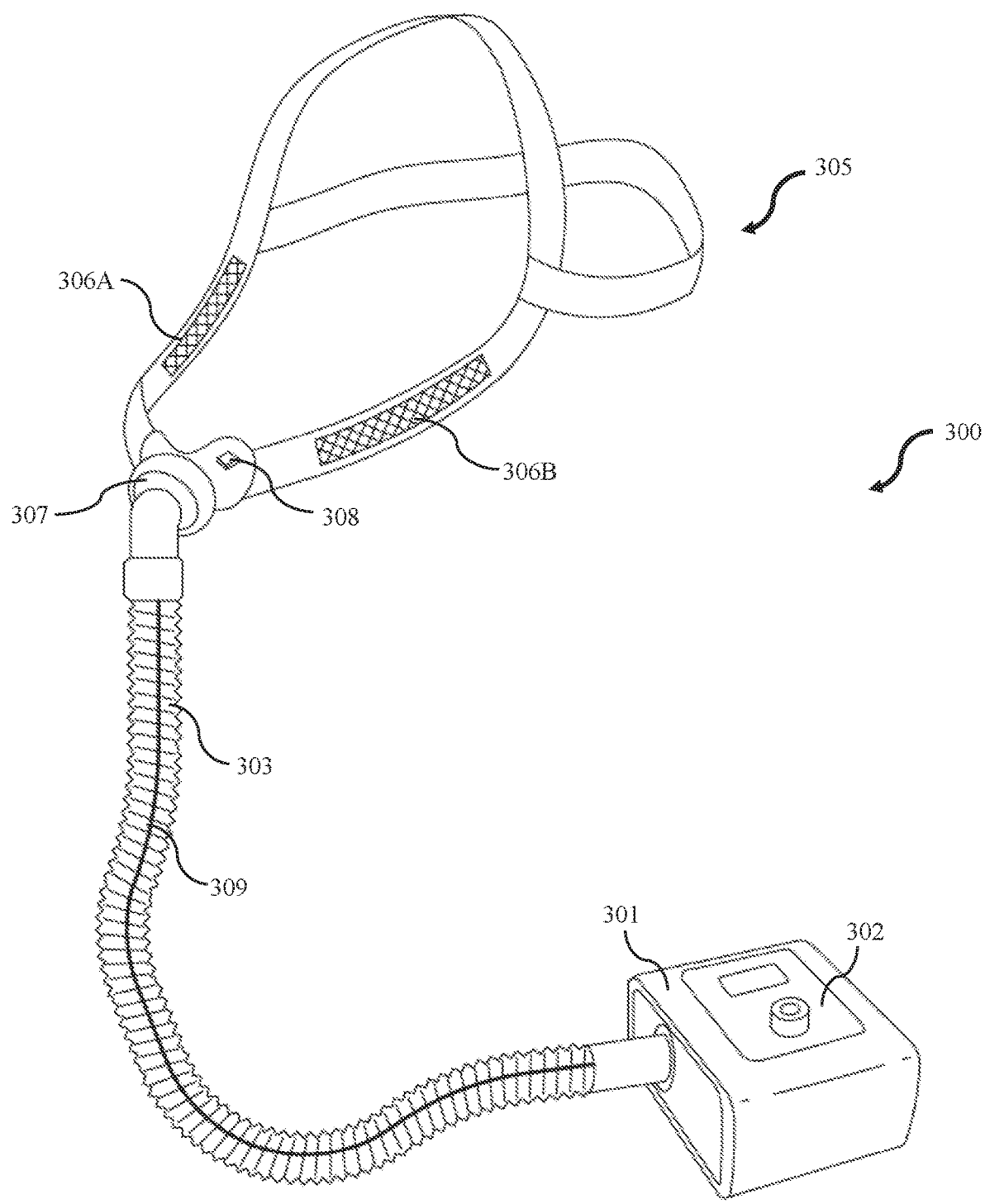
FIG. 3 illustrates a perspective view of the automatic shutoff CPAP system, wherein tension sensors are disposed on the headgear, in accordance with embodiments of the present disclosure.

Referring now to FIG. 3, shown is a perspective view of the automatic shutoff CPAP system 300, wherein tension sensors are disposed on the headgear, in accordance with embodiments of the present disclosure. CPAP system 300 includes a pair of sensors 306A, 306B (collectively referred to as 306) disposed on lateral sides of the headgear 305. In the illustrative embodiment, sensors 306A, 306B are configured as tension sensors. The sensors 306 are operably connected to processor 302 via a transmission wire 309 disposed within air tube 303. In the illustrative embodiment, the air mask 307 is configured as a nasal pillow. However, in some embodiments, air mask 307 may be any type of suitable air mask 307, such as an oral mask that covers the mouth. In the illustrative embodiment, air mask 307 includes a switch 308 that is operably connected to the processor 302.

In some embodiments, switch 308 may be configured to zero out sensor data received from sensor 306 when the headgear 305 is placed on a user's head. For example, the tension sensor data generated from sensor 306A, 306B may be variable because of the user's head size; therefore, zeroing out the data once the headgear 305 is placed on the head of a user may be necessary to ensure that the CPAP system is deactivated appropriately (e.g., only when the user takes off the headgear 305). In some embodiments the switch 308 may be configured to selectively activate the air pump 301 from the air mask 307. In this way, a user does not have to manually start the CPAP system 300 from the air pump 301. For example, the user may activate the air pump 301 via the switch 308 on the air mask 307 while lying in bed, preventing the user from having to get out of bed to activate the pump.

Figure 4A:
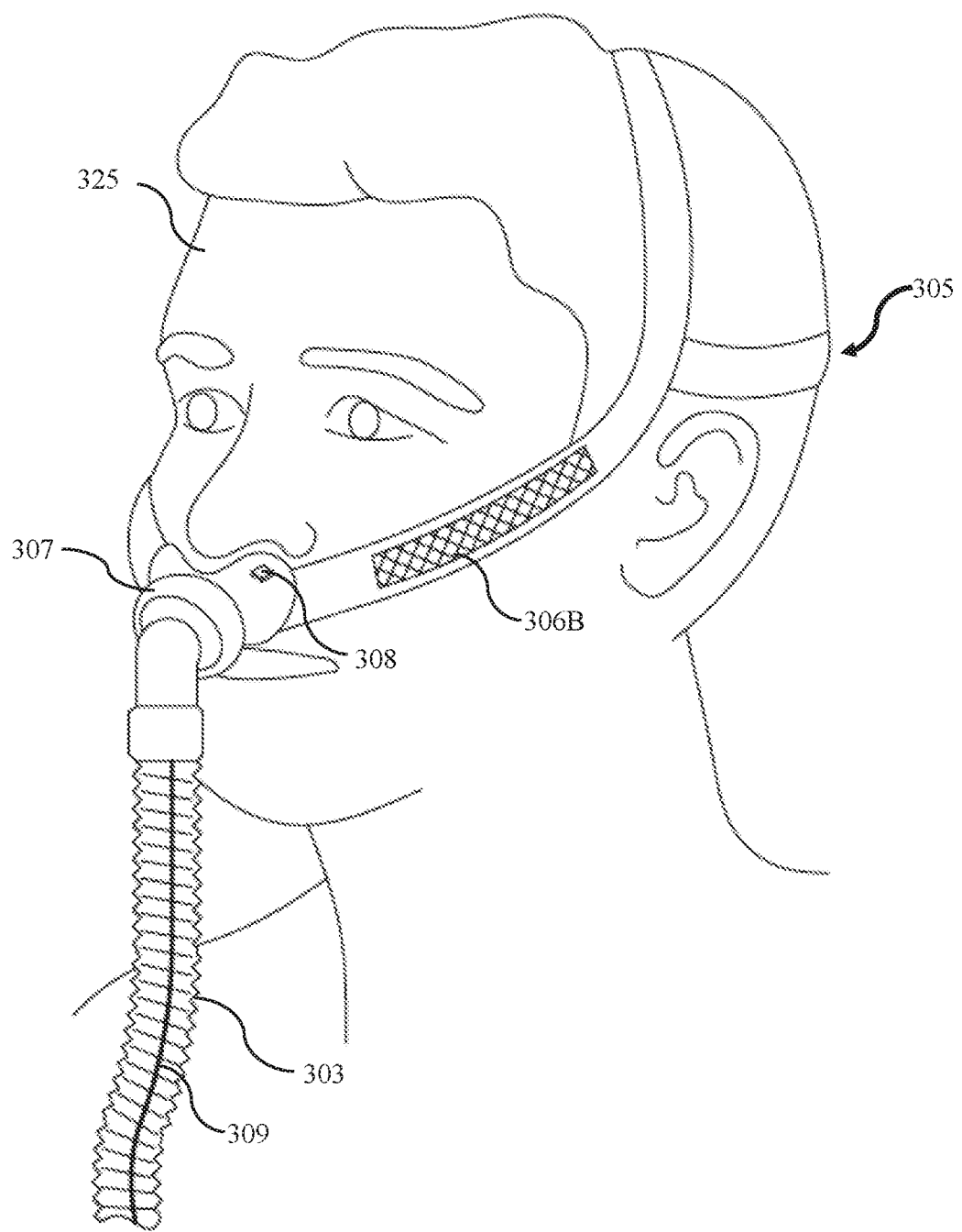
FIG. 4A illustrates a perspective view of the headgear, wherein tension sensors are in a relaxed position, in accordance with embodiments of the present disclosure.

Referring now to FIG. 4A, shown is a perspective view of the headgear 305, wherein tension sensors are in a relaxed position, in accordance with embodiments of the present disclosure. When headgear 305 is secured to the head of a user 325, the tension sensors 306A (not shown), 306B remain in a relaxed position, such that they are not fully expanded. Depending on the user's head size, the tension sensor data generated from tension sensors 306A, 306B may be zeroed when initially placed on the user's head. Zeroing the tension sensor data will account for any differences in expansion of the tension sensor when in a relaxed position on the head of the user 325. Once the tension sensor is zeroed, the air pump (not shown) may be activated by a user. Once activated, the processor of the CPAP system will continue to monitor data generated from tension sensors 306B via the transmission wire 309 disposed in air tube 303.

Figure 4B:
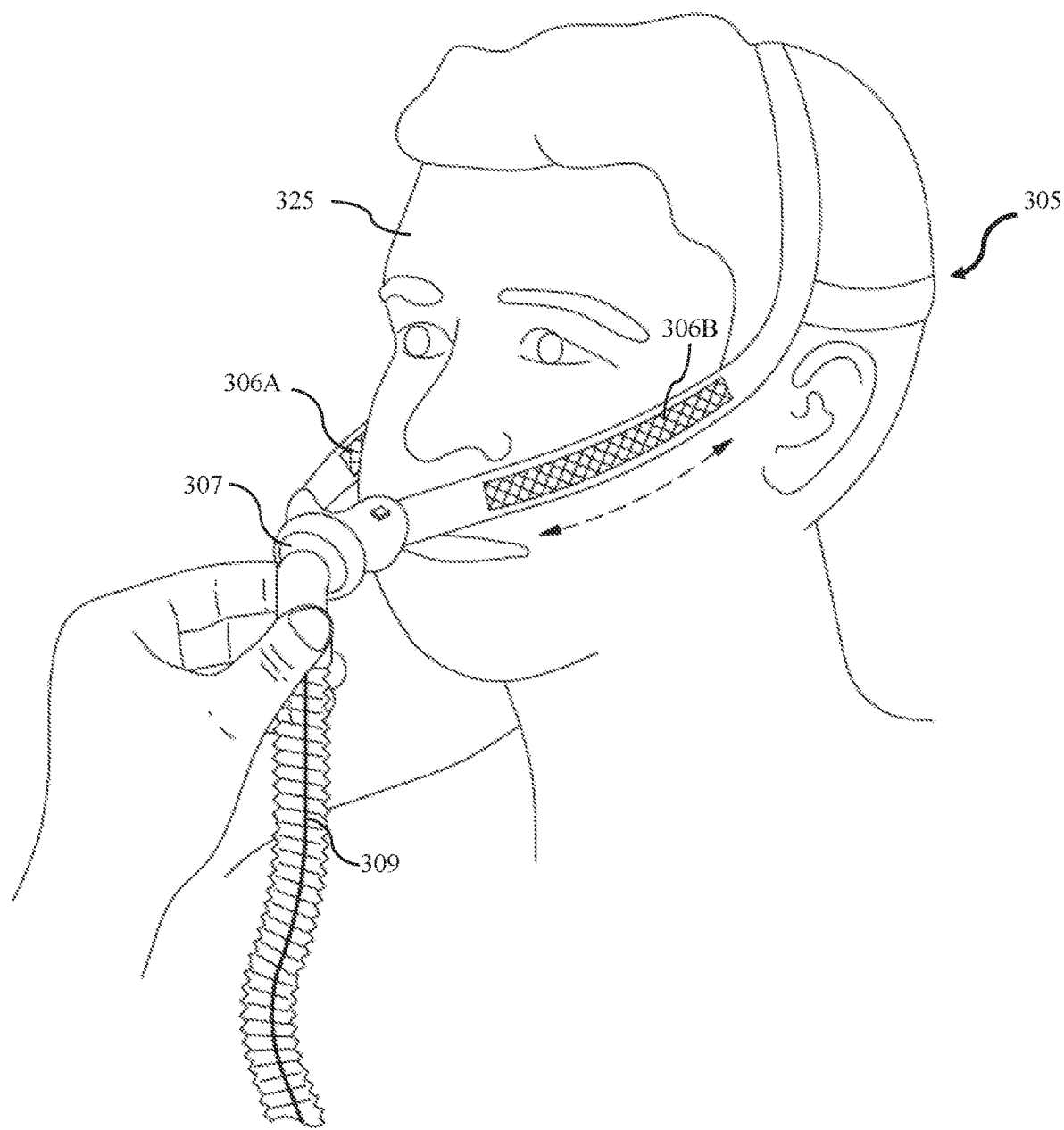
FIG. 4B illustrates a perspective view of the headgear, wherein tension sensors are in an expanded position, in accordance with embodiments of the present disclosure.

Referring now to FIG. 4B, shown is a perspective view of the headgear 305, wherein tension sensors are in an expanded position, in accordance with embodiments of the present disclosure. In the illustrative embodiment, the user removes air mask 307 by pulling the air mask outwardly from the face of the user 325. When the air mask 307 is pulled outwardly, the tension sensors 306A, 306B embedded in the lateral sides of the headgear 305 are placed in an expanded position. Data generated from the tension sensors is sent to the processor (not shown) through transmission wire 309. The data is analyzed by the processor, wherein the processor instructs the air pump to deactivate when the air mask 307 is removed by the user 325. Deactivating the air pump prevents compressed air from continuously flowing from the air mask 307.

Figure 5:
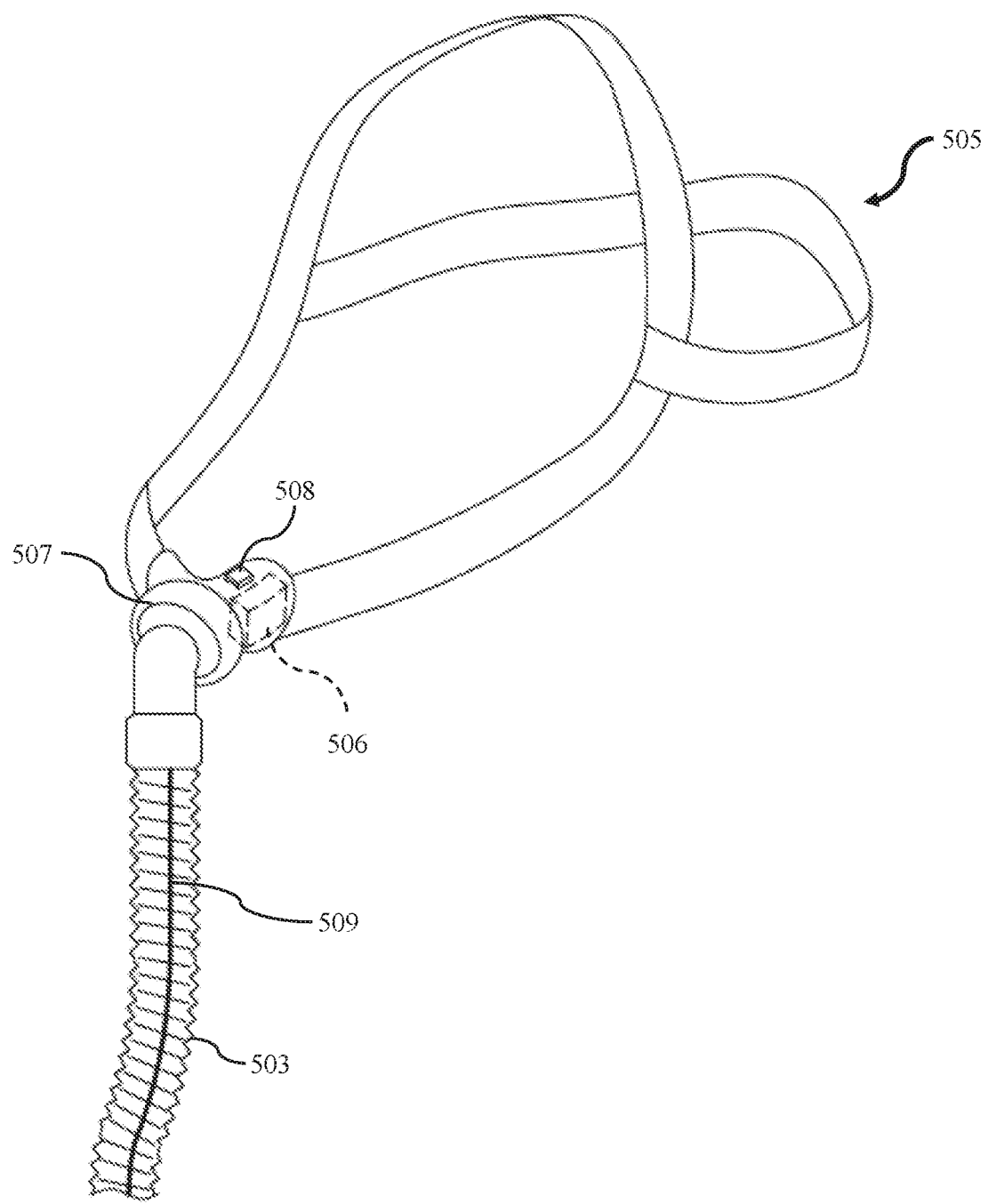
FIG. 5 illustrates a perspective view of the headgear, wherein an air pressure sensor is disposed within the air mask, in accordance with embodiments of the present disclosure.

Referring now to FIG. 5, shown is a perspective view of the headgear 505, wherein an air pressure sensor 506 is disposed within the air mask 507, in accordance with embodiments of the present disclosure. In the illustrated embodiment, sensor 506 is configured as an air pressure sensor. The air pressure sensor may be embedded in any suitable location such that an accurate air pressure reading may be obtained within the air mask 507. In the illustrative embodiment, the air mask 507 is configured as a nasal mask. In some embodiments, the air mask 507 may be configured as any type of suitable air mask, such as an oral mask. Sensor 506 is operably connected to the processor (not shown) of the CPAP system via transmission wire 509 disposed within air tube 503. Switch 508 is configured to zero or clear air pressure sensor data generated from sensor 506. In this way, the generated air pressure data from the air pressure sensor 506 can accurately account for variables relating to breathing and oral/naval cavity sizes of a user. In some embodiments, switch 508 may be configured to activate the air pump.

Figure 6A:
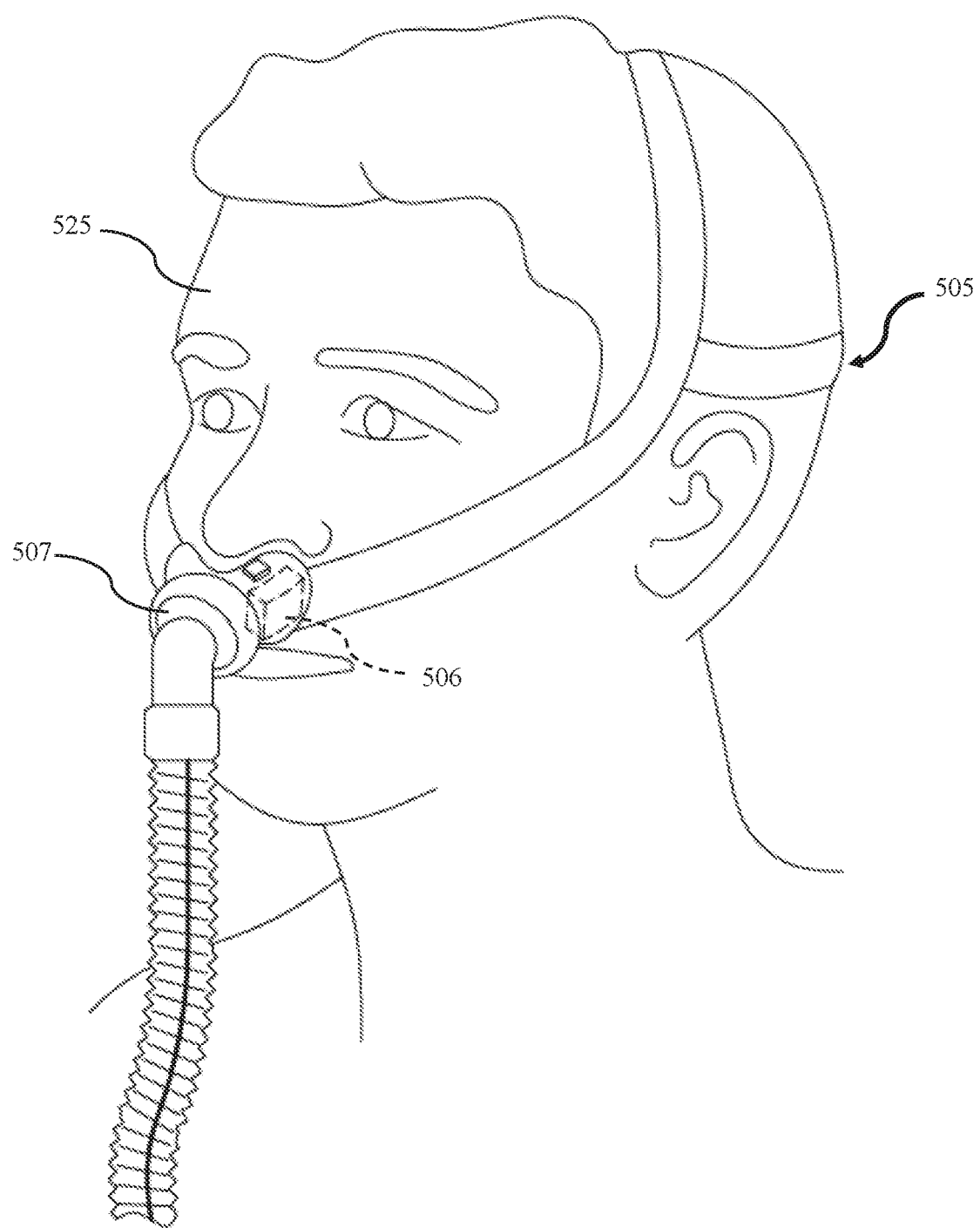
FIG. 6A illustrates a perspective view of the headgear secured to a user, wherein an air pressure sensor is embedded within the air mask, in accordance with embodiments of the present disclosure.

Referring now to FIG. 6A, shown is a perspective view of the headgear 505 secured to a user 525, wherein an air pressure sensor is embedded within the air mask, in accordance with embodiments of the present disclosure. Headgear 505 includes an air mask 507 having a sensor 506 embedded therein. In the illustrative embodiment, the sensor 506 is configured as an air pressure sensor. When in an operational position, the headgear 505 is secured to the head of the user 525 while the air mask 507 is placed tightly over the nasal cavity. Once secured, the user may activate the air pump (not shown) of the automatic shutoff CPAP system. Once activated, the processor (not shown) begins monitoring air pressure data received from the air pressure sensor 506.

Figure 6B:
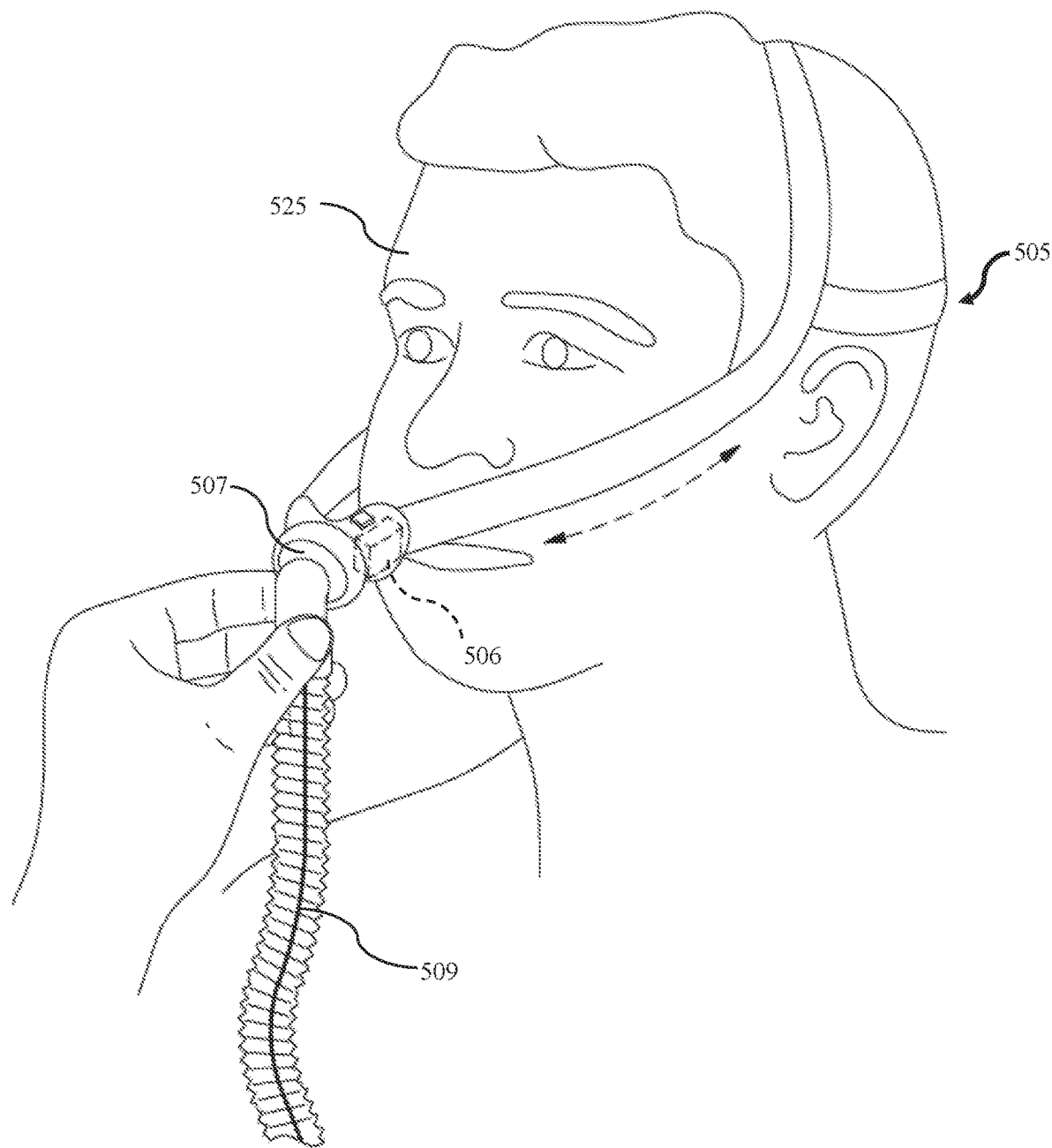
FIG. 6B illustrates a perspective view of the headgear removed from a user, wherein an air pressure sensor is embedded within the air mask, in accordance with embodiments of the present disclosure.

Referring now to FIG. 6B, shown is a perspective view of the headgear 505 removed from a user 525, wherein an air pressure sensor is embedded within the air mask, in accordance with embodiments of the present disclosure. In the illustrated embodiment, the air mask 507 is pulled outwardly from the face of the user 525, such that the air pressure drops within the air mask 507. Once the mask is removed, the air pressure sensor 506 embedded in the air mask 507 generates data that is transmitted to the processor (not shown). The processor determines whether the generated air pressure data is below a minimum air pressure threshold. If the generated air pressure data is below the threshold, the processor will instruct the air pump of the CPAP system to deactivate.

For example, the air pump of the CPAP system produces a continuous positive air pressure within the air mask when tightly secured on the face of the user. Once the masked is removed from the face, the sensor 506 will detect a significant drop in air pressure signaling the pump to deactivate. Alternatively, if the generated air pressure data is above the minimum air pressure threshold, the air pump will remain active while the processor continues to monitor the generated data from the air pressure sensor. For example, while in use, the air mask 507 may be slightly shifted on the face of the user 525 (e.g., shifting from movement during sleep). The air pressure data generated by the sensor 506 may fluctuate during movement, but the predetermined air pressure threshold may not be met, thus leaving the air pump active. In this way, the processor will only deactivate the air pump when there is a significant drop in air pressure detected by the air pressure sensor 506, preventing inadvertent deactivation of the system during sleep.

Figure 7:
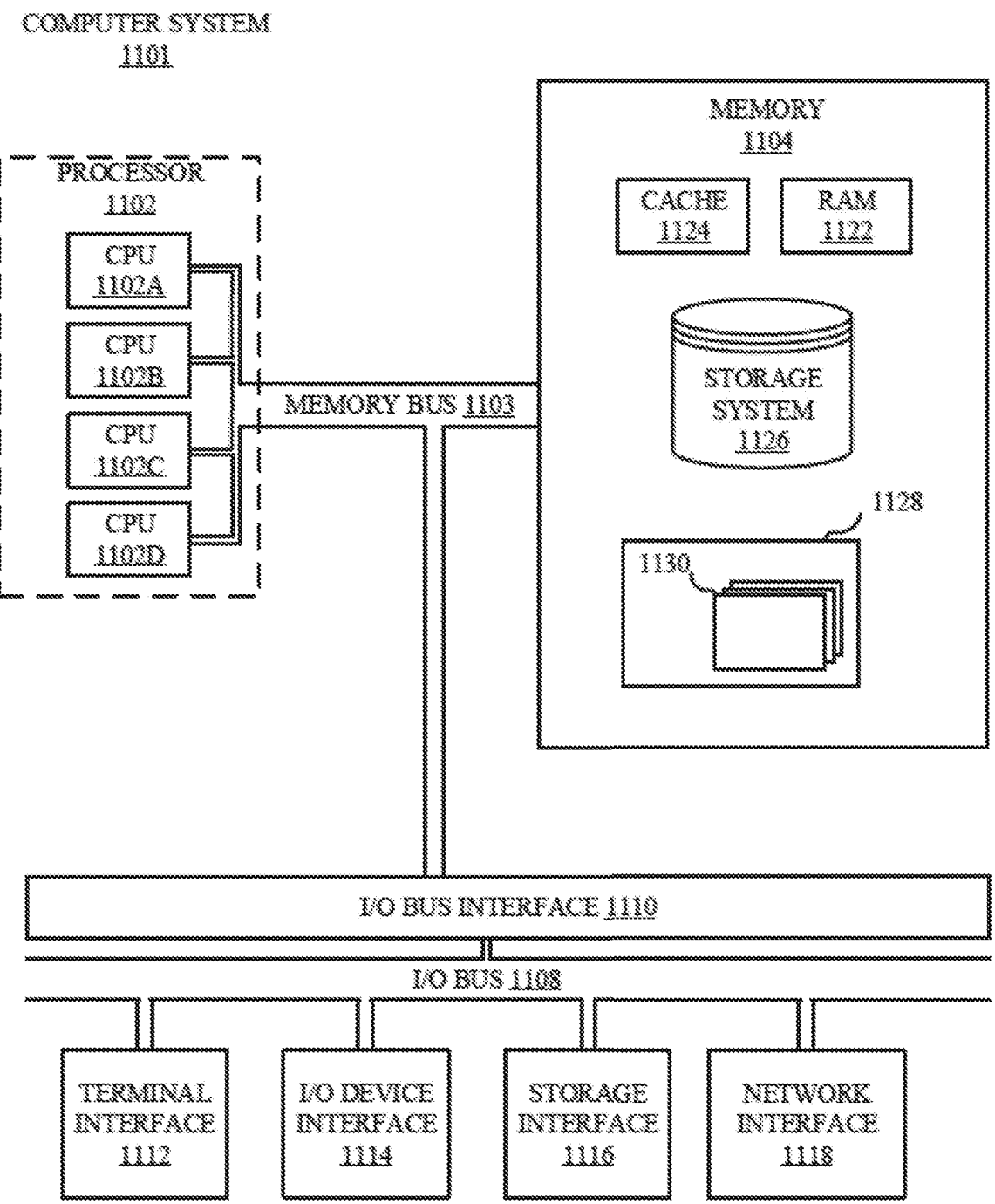
FIG. 7 illustrates a high-level block diagram of an example computer system that may be used in implementing one or more of the methods, tools, and modules, and any related functions, described herein, in accordance with embodiments of the present disclosure.

Referring now to FIG. 7, shown is a high-level block diagram of an example computer system 1101 that may be used in implementing one or more of the methods, tools, and modules, and any related functions, described herein (e.g., using one or more processor circuits or computer processors of the computer), in accordance with embodiments of the present disclosure. In some embodiments, the major components of the computer system 1101 may comprise one or more CPUs 1102, a memory subsystem 1104, a terminal interface 1112, a storage interface 1116, an I/O (Input/Output) device interface 1114, and a network interface 1118, all of which may be communicatively coupled, directly or indirectly, for inter-component communication via a memory bus 1103, an I/O bus 1108, and an I/O bus interface unit 1110.

The computer system 1101 may contain one or more general-purpose programmable central processing units (CPUs) 1102A, 1102B, 1102C, and 1102D, herein generically referred to as the CPU 1102. In some embodiments, the computer system 1101 may contain multiple processors typical of a relatively large system; however, in other embodiments the computer system 1101 may alternatively be a single CPU system. Each CPU 1102 may execute instructions stored in the memory subsystem 1104 and may include one or more levels of on-board cache. In some embodiments, a processor can include at least one or more of, a memory controller, and/or storage controller. In some embodiments, the CPU can execute the processes included herein (e.g., process 200).

System memory 1104 may include computer system readable media in the form of volatile memory, such as random access memory (RAM) 1122 or cache memory 1124. Computer system 1101 may further include other removable/non-removable, volatile/non-volatile computer system data storage media. By way of example only, storage system 1126 can be provided for reading from and writing to a non-removable, non-volatile magnetic media, such as a "hard drive." Although not shown, a magnetic disk drive for reading from and writing to a removable, non-volatile magnetic disk (e.g., a "floppy disk"), or an optical disk drive for reading from or writing to a removable, non-volatile optical disc such as a CD-ROM, DVD-ROM or other optical media can be provided. In addition, memory 1104 can include flash memory, e.g., a flash memory stick drive or a flash drive. Memory devices can be connected to memory bus 1103 by one or more data media interfaces. The memory 1104 may include at least one program product having a set (e.g., at least one) of program modules that are configured to carry out the functions of various embodiments.

Although the memory bus 1103 is shown in FIG. 7 as a single bus structure providing a direct communication path among the CPUs 1102, the memory subsystem 1104, and the I/O bus interface 1110, the memory bus 1103 may, in some embodiments, include multiple different buses or communication paths, which may be arranged in any of various forms, such as point-to-point links in hierarchical, star or web configurations, multiple hierarchical buses, parallel and redundant paths, or any other appropriate type of configuration. Furthermore, while the I/O bus interface 1110 and the I/O bus 1108 are shown as single units, the computer system 1101 may, in some embodiments, contain multiple I/O bus interface units 1110, multiple I/O buses 1108, or both. Further, while multiple I/O interface units are shown, which separate the I/O bus 1108 from various communications paths running to the various I/O devices, in other embodiments some or all of the I/O devices may be connected directly to one or more system I/O buses.

In some embodiments, the computer system 1101 may be a multi-user mainframe computer system, a single-user system, or a server computer or similar device that has little or no direct user interface, but receives requests from other computer systems (clients). Further, in some embodiments, the computer system 1101 may be implemented as a desktop computer, portable computer, laptop or notebook computer, tablet computer, pocket computer, telephone, smart phone, network switches or routers, or any other appropriate type of electronic device.

It is noted that FIG. 7 is intended to depict the representative major components of an exemplary computer system 1101. In some embodiments, however, individual components may have greater or lesser complexity than as represented in FIG. 7, components other than or in addition to those shown in FIG. 7 may be present, and the number, type, and configuration of such components may vary.

One or more programs/utilities 1128, each having at least one set of program modules 1130 may be stored in memory 1104. The programs/utilities 1128 may include a hypervisor (also referred to as a virtual machine monitor), one or more operating systems, one or more application programs, other program modules, and program data. Each of the operating systems, one or more application programs, other program modules, and program data or some combination thereof, may include an implementation of a networking environment. Programs 1128 and/or program modules 1130 generally perform the functions or methodologies of various embodiments.

As discussed in more detail herein, it is contemplated that some or all of the operations of some of the embodiments of methods described herein may be performed in alternative orders or may not be performed at all; furthermore, multiple operations may occur at the same time or as an internal part of a larger process.

The present disclosure may be a system, a method, and/or a computer program product. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the various embodiments. As used herein, the singular forms "a," "an," and "the" are intended to include the plural forms as well, unless the context clearly indicates otherwise. It will be further understood that the terms "includes" and/or "including," when used in this specification, specify the presence of the stated features, integers, steps, operations, elements, and/or components, but do not preclude the presence or addition of one or more other features, integers, steps, operations, elements, components, and/or groups thereof. In the previous detailed description of example embodiments of the various embodiments, reference was made to the accompanying drawings (where like numbers represent like elements), which form a part hereof, and in which is shown by way of illustration specific example embodiments in which the various embodiments may be practiced. These embodiments were described in sufficient detail to enable those skilled in the art to practice the embodiments, but other embodiments may be used and logical, mechanical, electrical, and other changes may be made without departing from the scope of the various embodiments. In the previous description, numerous specific details were set forth to provide a thorough understanding of the various embodiments. But, the various embodiments may be practiced without these specific details. In other instances, well-known circuits, structures, and techniques have not been shown in detail in order not to obscure embodiments.

Different instances of the word "embodiment" as used within this specification do not necessarily refer to the same embodiment, but they may. Any data and data structures illustrated or described herein are examples only, and in other embodiments, different amounts of data, types of data, fields, numbers and types of fields, field names, numbers and types of rows, records, entries, or organizations of data may be used. In addition, any data may be combined with logic, so that a separate data structure may not be necessary. The previous detailed description is, therefore, not to be taken in a limiting sense.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Although the present disclosure has been described in terms of specific embodiments, it is anticipated that alterations and modification thereof will become apparent to those skilled in the art. Therefore, it is intended that the following claims be interpreted as covering all such alterations and modifications as fall within the true spirit and scope of the disclosure.

What is claimed is:

1. An automatic shutoff continuous positive air pressure (CPAP) system, comprising:
    an air pump;
    headgear including an air mask;
    a sensor disposed on the headgear; and
    a processor, wherein the processor is configured to perform a method, the method comprising:
        setting a shutoff threshold for the sensor in response to a user pressing a communicatively coupled switch while pulling the air mask away from a face of the user;
        monitoring data generated from the sensor;
        comparing the generated data to the shutoff threshold;
        determining, in response to the generated data satisfying the shutoff threshold, that the air mask has been pulled away from the face of the user; and
        deactivating, in response to determining that the air mask has been pulled away from the face of the user, the air pump.

2. The automatic shutoff CPAP system of claim 1, wherein the method performed by the processor further comprises:
    zeroing out data generated from the sensor in response to the user pressing the communicatively coupled switch; and
    receiving user specific data from the sensor, wherein the user specific data indicates the user is wearing the air mask.

3. The automatic shutoff CPAP system of claim 1, wherein the sensor is a tension sensor and the shutoff threshold is a predetermined maximum tension threshold.

4. The automatic shutoff CPAP system of claim 3, wherein the tension sensor is disposed on a lateral side of a strap of the headgear.

5. The automatic shutoff CPAP system of claim 1, wherein the sensor is an air pressure sensor and the shutoff threshold is a predetermined minimum air pressure threshold.

6. The automatic shutoff CPAP system of claim 5, wherein the air pressure sensor is disposed in the air mask of the headgear.

7. A method for automatically deactivating an air pump of a continuous positive air pressure (CPAP) system, the method comprising:
    monitoring, by a processor, data generated from a tension sensor disposed on a lateral side of a strap of headgear of a CPAP system;
    comparing, by the processor, the generated data to a predetermined maximum tension shutoff threshold;
    determining, by the processor and in response to the generated data satisfying the predetermined maximum tension shutoff threshold, that an air mask of the headgear has been pulled away from a face of a user; and
    deactivating, by the processor and in response to determining that the air mask has been pulled away from the face of the user, an air pump of the CPAP system.

8. The method of claim 7, further comprising:
    zeroing, by the processor, data generated from the tension sensor in response to the user pressing a communicatively coupled switch; and
    receiving, by the processor, user specific data from the tension sensor, wherein the user specific data indicates the user is wearing the air mask.

9. The method of claim 7, further comprising:
    setting, by the processor, the predetermined maximum tension shutoff threshold in response to the user pressing a communicatively coupled switch while pulling the air mask away from the face of the user.

10. A computer program product comprising a non-transitory computer readable storage medium having program instructions embodied therewith, the program instructions executable by a processor to cause the processor to perform a method comprising:
    setting a shutoff threshold for a sensor disposed on headgear of a CPAP system in response to a user pressing a communicatively coupled switch while pulling an air mask included in the headgear away from a face of the user;
    monitoring data generated from the sensor;
    comparing the generated data to the shutoff threshold;
    determining, in response to the generated data satisfying the shutoff threshold, that the air mask of the headgear has been pulled away from the face of the user; and
    deactivating, in response to determining that the air mask has been pulled away from the face of the user, an air pump of the CPAP system.

11. The computer program product of claim 10, wherein the method performed by the processor further comprises:
    zeroing data generated from the sensor in response to the user pressing the communicatively coupled switch; and
    receiving user specific data from the sensor, wherein the user specific data indicates the user is wearing the air mask.

12. The computer program product of claim 10, wherein the sensor is a tension sensor and the shutoff threshold is a predetermined maximum tension threshold.

13. The computer program product of claim 10, wherein the sensor is an air pressure sensor and the shutoff threshold is a predetermined minimum air pressure threshold.

14. The computer program product of claim 13, wherein the air pressure sensor is disposed in the air mask of the headgear.

* * * * *